US006733516B2

(12) United States Patent
Simons et al.

(10) Patent No.: US 6,733,516 B2
(45) Date of Patent: *May 11, 2004

(54) METHOD AND APPARATUS FOR LIMITING REVASCULARIZATION TO VIABLE TISSUE

(75) Inventors: Pamela P. Simons, Bothell, WA (US); Brandon Shuman, Kirkland, WA (US); Lee A. Holzapfel, Maple Grove, MN (US)

(73) Assignee: SciMed Life Systems, Inc., Maple Grove, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/765,209

(22) Filed: Jan. 17, 2001

(65) Prior Publication Data

US 2002/0095145 A1 Jul. 18, 2002

(51) Int. Cl.[7] .................................................. A61B 18/18
(52) U.S. Cl. .............................. 606/634; 606/42; 606/49
(58) Field of Search ................................ 606/32–34, 41, 606/42; 607/2, 5, 8, 101, 100; 600/515

(56) References Cited

U.S. PATENT DOCUMENTS

| 5,282,840 A | 2/1994 | Hudrlik |
| 5,341,807 A | 8/1994 | Nardella |
| 5,447,529 A | 9/1995 | Marchlinski et al. |
| 5,562,721 A | 10/1996 | Marchlinski et al. |
| 5,573,533 A | 11/1996 | Strul |
| 5,673,704 A | 10/1997 | Marchlinski et al. |
| 5,725,521 A | 3/1998 | Mueller |
| 5,743,903 A | 4/1998 | Stern et al. |
| 6,042,581 A | 3/2000 | Ryan et al. |
| 6,093,185 A | 7/2000 | Ellis et al. |
| 6,123,702 A | 9/2000 | Swanson et al. |
| 6,156,031 A | 12/2000 | Aita et al. |
| 6,162,216 A | 12/2000 | Guziak et al. |
| 6,212,426 B1 * | 4/2001 | Swanson .................... 600/510 |

* cited by examiner

*Primary Examiner*—Rosiland K. Rollins
(74) *Attorney, Agent, or Firm*—Christensen O'Connor Johnson Kindness PLLC

(57) ABSTRACT

A method and apparatus for limiting the application of ablation energy to viable myocardial tissue. An ablation energy generator produces a test signal that is applied to the heart muscle. The response of the heart muscle to the test signal is determined and used to analyze the viability of the heart tissue. If the heart muscle is viable, a higher powered ablation pulse may be delivered. If the tissue is not viable, no ablation energy is delivered. In one embodiment of the invention, the test signal is a low voltage, high frequency signal and the impedance of the tissue in response to the test signal is detected to determine tissue viability.

12 Claims, 4 Drawing Sheets

METHOD AND APPARATUS FOR LIMITING REVASCULARIZATION TO VIABLE TISSUE

FIELD OF THE INVENTION

The present invention relates to medical devices in general, and in particular to systems for performing myocardial revascularization.

BACKGROUND OF THE INVENTION

Myocardial revascularization is a surgical technique whereby small holes or craters are created in the myocardium to allow oxygenated blood within the ventricle to contact the myocardium. One technique, called transmyocardial revascularization (TMR), involves routing an energy delivery catheter through an opening in the chest wall to the exterior of the patient's heart muscle. Ablation energy is then delivered to the catheter to create a hole that extends from the epicardium, or exterior of the patient's heart, to the interior of the ventricle such that oxygenated blood flows into and out of the holes. These holes rapidly seal at the outside of the heart but remain open towards the interior of the ventricle. Another technique, called percutaneous myocardial revascularization (PMR), utilizes an energy delivery catheter that is routed through a patient's vasculature to the interior wall of the left ventricle. Ablation energy is then supplied to the ventricular wall to remove a portion of the endocardium and expose a portion of the myocardium to oxygenated blood flow.

Myocardial revascularization is most often used when an area of the myocardium is not receiving adequate blood flow because of clots or diseases that inhibit the ability of the vessels to supply blood to the heart. It is not known whether the procedure induces new blood vessels to form in the myocardium or simply deadens nerve endings in the myocardium to alleviate patient discomfort.

Not all cardiac tissue can be helped using myocardial revascularization. For example, if the myocardial tissue has been deprived of oxygenated blood for too long, it may be dead and no benefits to the tissue will be obtained if treated. Applying ablation energy to such myocardial tissue is not only a waste of time, but the tissue may be more susceptible to ventricular perforation. To increase the efficiency and efficacy of a myocardial revascularization procedure, there is a need for a system that can guide a physician to only perform a myocardial revascularization procedure in viable cardiac tissue.

SUMMARY OF THE INVENTION

The present invention is a method and apparatus for limiting the delivery of ablation energy to viable areas of the myocardium. An energy delivery catheter is routed to the patient's myocardium. A determination is made if the myocardium adjacent to the distal end of the catheter is viable and, if so, ablation energy is delivered through the catheter to the myocardial wall. If the tissue adjacent the distal end of the energy delivery catheter is not viable, then no ablation energy is delivered.

In one embodiment of the invention, tissue viability is determined by applying a test signal to the tissue and measuring the impedance of the tissue in response to the test signal applied. If the impedance is greater than a predefined amount, the tissue is deemed not to be viable. Therefore, no ablation energy will be delivered.

The energy delivery catheter may be routed through the patient's vasculature or through an opening in the patient's chest wall.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
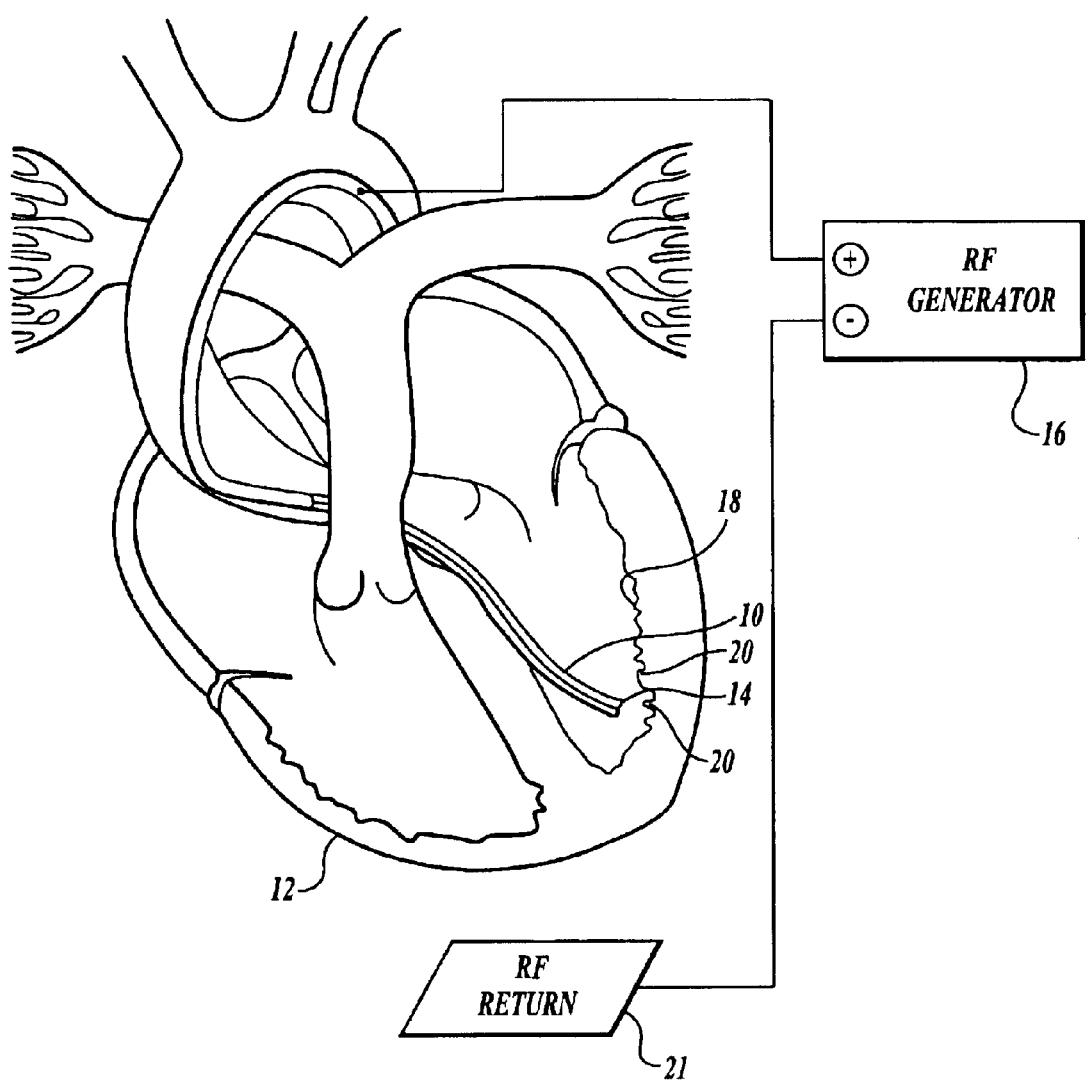
FIG. 1 illustrates a system for performing myocardial revascularization according to the present invention.

FIG. 1 illustrates the major components of the presently preferred system for performing PMR according to the present invention. A steerable catheter 10 is routed through a patient's vasculature and into the left ventricle of the heart 12. In order to route the steerable catheter to the left ventricle, an incision is made into a patient's femoral artery and an introducer sheath approximately 12" long (not shown) is introduced into the wound. Next, the steerable catheter 10 is advanced along the vasculature until it nears the patient's heart valve. A "pig tail" catheter (also not shown) is inserted into the steerable catheter 10 in order to push past a valve at the entrance of the left ventricle. The pig tail catheter is removed and an inner catheter (described below) including an energy delivery catheter 14 is advanced along the steerable catheter 10 into the left ventricle.

The energy delivery catheter 14 delivers ablation energy produced by an ablation energy source 16. In the currently preferred embodiment, the ablation energy source 16 is a radio frequency (RF) voltage generator that is controlled to selectively supply RF electrical energy to the energy delivery catheter 14. When the distal end of the energy delivery catheter 14 is adjacent to, or in contact with, an ischemic region 18 of the left ventricle, a physician triggers the RF voltage generator to supply a 400 millisecond radio frequency pulse to the energy delivery catheter 14. The ablation energy is delivered to the interior of the heart muscle to ablate or remove a portion of the endocardial, or inner lining of the heart, thereby creating regions or craters 20 where the myocardium is exposed. The exposed myocardium is then in contact with the oxygenated blood that is flowing within the left ventricle. The delivery of the RF pulses can take place independently of the cardiac cycle.

In the presently preferred embodiment PMR device, the energy delivery catheter 14 is a unipolar device including a single electrode. A return electrode 21 is positioned on the exterior of the patient to provide a current path back to the RF voltage generator.

Figure 2:
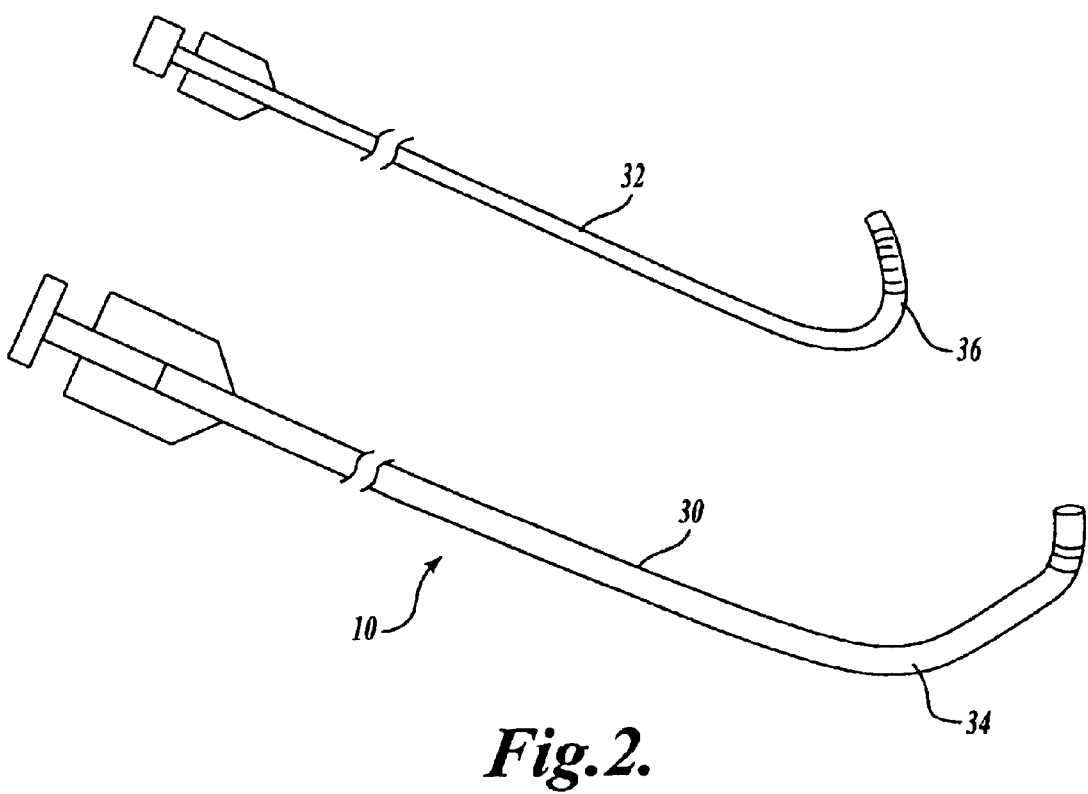
FIG. 2 illustrates a pair of catheters that are used to position an energy delivery catheter at a desired location in the patient's heart.

FIG. 2 illustrates the presently preferred steerable catheter 10 that routes the energy delivery catheter 14 into the patient's heart muscle. The steerable catheter 10 comprises an outer catheter 30 and inner catheter 32 that are relatively flexible at their distal ends. The outer catheter 30 has a predefined "J-shaped" bend 34 at its distal end, and the inner catheter 32 has a predefined "J-shaped" bend 36 at its distal end. The radius of the bend 36 is smaller than that of the bend 34. Each of the catheters 30, 32 has a connector at its proximal end with a pair of opposed "wings" or tabs on it. The diameter of the inner catheter 32 is selected such that it can be threaded into a lumen that extends along the length of the outer catheter 30. When the inner catheter 32 is inserted into the outer catheter 30, the tabs on the proximal ends of the catheters allow the inner catheter 32 to be rotated with respect to the outer catheter 30. The predefined bends 34 and 36 cooperate to vary the orientation of a distal tip 38 of the inner catheter 32. The bends 34 and 36 may be aligned so they both bend in the same direction, in opposite directions, or at any position in between.

Figure 3:
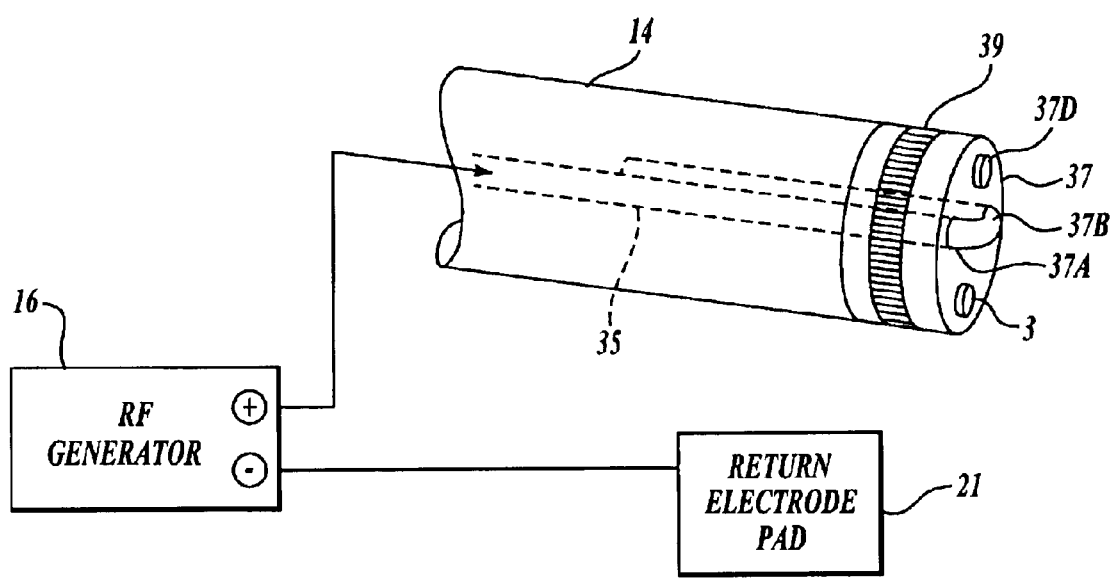
FIG. 3 illustrates in further detail the energy delivery catheter used in one embodiment of the present invention to deliver the ablation energy.

As illustrated in FIG. 3 above, the energy delivery catheter 14 houses a flexible electrode 35. The electrode 35 is threaded through two holes of a ceramic cap 37 at the distal end of the catheter 14. Specifically, the electrode 35 exits a first hole 37a in the distal direction and then is routed proximally through a second hole 37b in the ceramic cap 37 such that a portion of the electrode 35 is exposed at the distal end of the catheter. The distal end of the electrode 35 does not extend all the way back along the length of the catheter 14 but terminates at a point generally near the distal end of the energy delivery catheter 14. The ceramic cap 37 may include a pair of additional holes 37c and 37d, that allow fluids such as dyes or drugs to be supplied through a lumen in the energy delivery catheter 14 and delivered to the ablation site. Finally, the energy delivery catheter 14 may include a radiopaque marker band 39 that surrounds the ceramic cap 37 in order to enhance the visibility of the energy delivery catheter 14 under fluoroscopy or other imaging techniques, as the PMR procedure is being performed.

Figure 4:
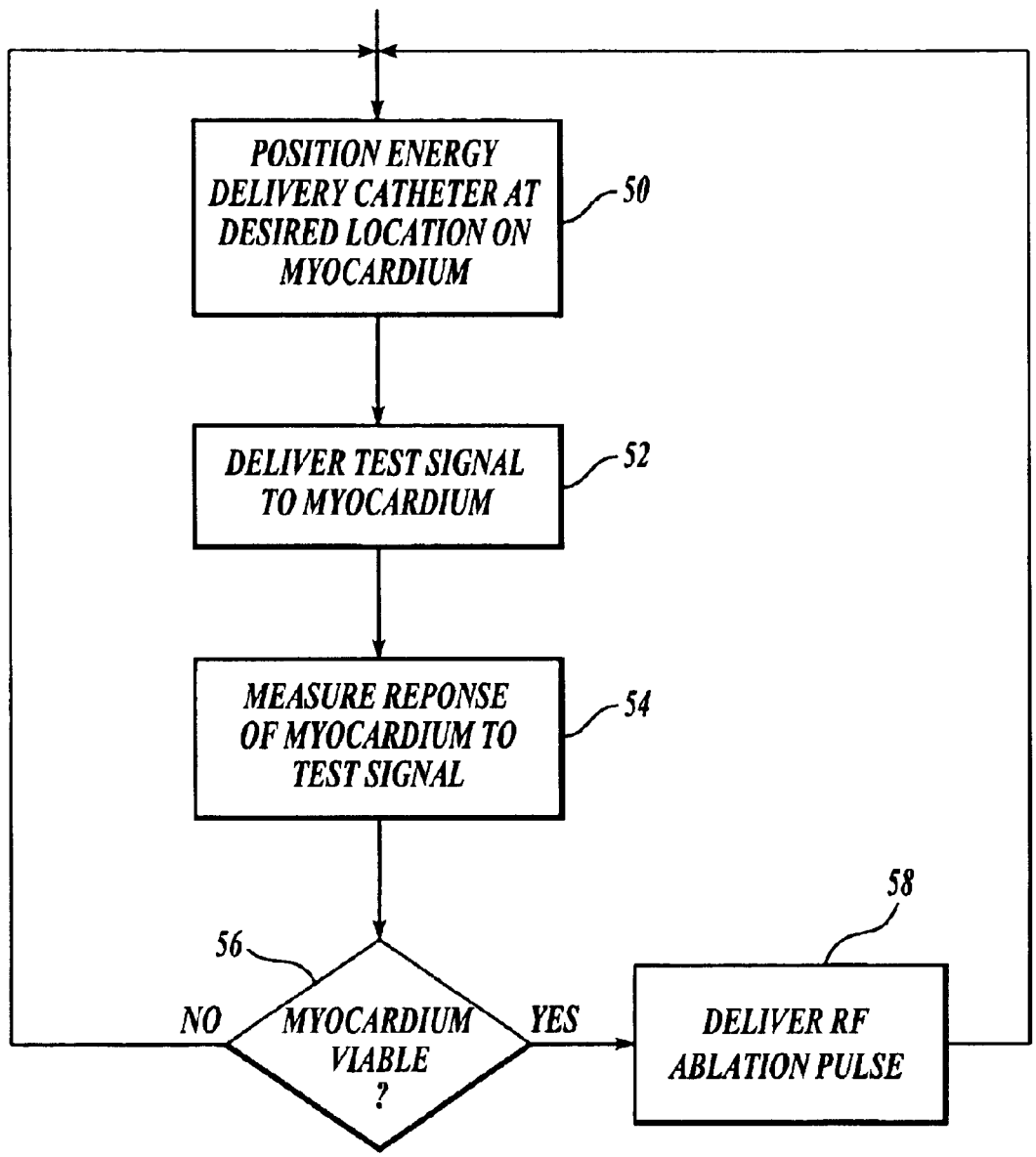
FIG. 4 is a flow chart of the steps performed by one embodiment of the present invention to limit the application of ablation energy to viable myocardial tissue.

As indicated above, to prohibit the application of ablation energy to myocardial tissue that would not benefit from the procedure, the present invention determines the viability of such tissue prior to the delivery of ablation energy. FIG. 4 illustrates a series of steps performed by the present invention to ensure that ablation energy is not applied to non-viable cardiac tissue. Beginning with a step 50, a physician positions the energy delivery catheter at the desired location on or inside the heart. As indicated above, the catheter may be placed either against the endocardial or epicardial layer of the heart muscle. At a step 52, a test signal is delivered to the heart muscle and the heart's response to the test signal is measured at a step 54.

From the results of the test signal, a decision is made at step 56 to determine whether the myocardium in the area adjacent the energy delivery catheter is viable. If the tissue is viable, the ablation energy is delivered at a step 58. If the tissue is not viable, the physician is prevented from delivering ablation energy to that spot on the ventricle. The physician then moves the probe and processing returns to step 50 as described above.

In the presently preferred embodiment of the invention, the test signal delivered at step 52 is a low energy, high frequency RF energy pulse. Preferably, the signal has a frequency greater than 50 kHz in order to avoid fibrillating the heart. The impedance of the heart muscle in response to the test signal delivered is the presently preferred criteria by which viability of the heart is determined at step 54.

If the impedance is greater than a predefined level, such as 1700 ohms, it is assumed that the heart muscle is dead or would otherwise not respond to the myocardial revascularization treatment, and no ablation energy is delivered at that point. In order to measure impedance, the ablation energy source 16 shown in FIG. 1 includes a circuit that determines the magnitude of the current received in response to the low power, RF test signal applied. Based on the magnitude of the current sensed, a switch or other control within the ablation energy source is inhibited from delivering an RF pulse to the cardiac tissue at that position. In the presently preferred embodiment of the invention, the test signal is delivered when the physician activates a foot pedal or other control to initiate the delivery of ablation energy. The test signal is delivered first and if the impedance indicates the tissue is viable, the ablation energy pulse follows immediately or very shortly thereafter.

Although the present invention uses a low energy, high frequency test signal in order to measure the impedance of the cardiac tissue, it will be appreciated that other criteria could be used to determine tissue viability. For example, the catheter may include an electrode or other sensor to determine if the cardiac tissue in the area of the electrode is responding to the heart's own pacing signals. If no tissue response is observed, no ablation energy will be applied to that portion of the heart muscle.

While the preferred embodiment of the invention has been illustrated and described, it will be appreciated that various changes can be made therein without departing from the scope of the invention. It is therefore intended that the scope of the invention be determined from the following claims and equivalents thereto.

The embodiments of the invention in which an exclusive property or privilege is claimed are defined as follows:

1. A system for performing myocardial ablation, comprising:
    a source of ablation energy;
    a test signal source;
    a catheter for delivering the ablation energy and test signal to a location in a patient's myocardium;
    a circuit for detecting a viability of the myocardium in response to the test signal and for selectively enabling the ablation energy source to deliver ablation energy to the patient's myocardium based on the viability of the myocardium to the test signal delivered.

2. The system of claim 1, wherein the test signal is a low voltage, high frequency signal.

3. The system of claim 1, wherein the ablation energy is RF energy.

4. The system of claim 3, wherein the circuit determines the impedance of the myocardium and enables the source of ablation energy to deliver an RF pulse if the impedance is below a predetermined threshold.

5. The system of claim 1, wherein the catheter is adapted to be routed into the interior of a left ventricle of the heart via the patient's vasculature.

6. The system of claim 1 wherein the catheter is adapted to be routed to an exterior of the heart via an opening in the patient's chest cavity.

7. A method for performing myocardial revascularization comprising the steps of:
    positioning an energy delivery catheter adjacent to a patient's myocardium;
    determining if the myocardial tissue adjacent a distal tip of the energy delivery catheter is viable; and
    ablating the myocardium by delivering an ablation pulse to the myocardium if the tissue is viable.

8. The method of claim 7, wherein the determination if the myocardium is viable is made by:
    delivering a test signal to an area of a heart muscle and monitoring the myocardium's response to the test signal delivered.

9. The method of claim 8, wherein the response is monitored by determining the impedance of the area of the heart muscle to the test signal.

10. The method of claim 7, wherein the energy delivery catheter is delivered through a patient's vasculature to an interior of the patient's ventricle.

11. A system for performing myocardial revascularization, comprising:
   an ablation energy source;
   a circuit for determining the viability of myocardial tissue and for selectively controlling the ablation energy source such that ablation energy is delivered to viable cardiac tissue; and
   a catheter for delivering ablation energy from the ablation energy source to a patient's myocardium.

12. The system of claim 11, wherein the circuit comprises:
   a source of a low power test signal; and
   an impedance measuring circuit that measures the impedance of the myocardial tissue in response to the low power test signal.

* * * * *